(12) United States Patent
Moeller et al.

(10) Patent No.: US 9,145,557 B2
(45) Date of Patent: Sep. 29, 2015

(54) OLIGONUCLEOTIDES FOR MODULATION OF TARGET RNA ACTIVITY

(75) Inventors: Thorleif Moeller, Arslev (DK); Christina Udesen, Arslev (DK)

(73) Assignee: MIRRX THERAPEUTICS A/S, Lyngby (DK)

( * ) Notice: Subject to any disclaimer, the term of this patent is extended or adjusted under 35 U.S.C. 154(b) by 0 days.

(21) Appl. No.: 13/989,128

(22) PCT Filed: Nov. 23, 2011

(86) PCT No.: PCT/DK2011/050447
§ 371 (c)(1),
(2), (4) Date: Oct. 15, 2013

(87) PCT Pub. No.: WO2012/069059
PCT Pub. Date: May 31, 2012

(65) Prior Publication Data
US 2014/0031537 A1    Jan. 30, 2014

(30) Foreign Application Priority Data
Nov. 23, 2010  (DK) ................................. 2010 01061

(51) Int. Cl.
*C07H 21/04*  (2006.01)
*C12N 15/113*  (2010.01)
*C07H 21/00*  (2006.01)

(52) U.S. Cl.
CPC .............. *C12N 15/113* (2013.01); *C07H 21/00* (2013.01); *C12N 2310/141* (2013.01); *C12N 2310/314* (2013.01); *C12N 2310/321* (2013.01); *C12N 2310/322* (2013.01); *C12N 2310/3233* (2013.01); *C12N 2310/3521* (2013.01); *C12N 2310/3525* (2013.01); *C12N 2310/3533* (2013.01)

(58) Field of Classification Search
None
See application file for complete search history.

(56) References Cited

U.S. PATENT DOCUMENTS 8,637,655 B2 * 1/2014 Mulero et al. ............. 536/24.33
2003/0165859 A1 * 9/2003 Nazarenko et al. ............... 435/6
2011/0178283 A1 * 7/2011 Rigoutsos et al. ........... 536/24.5

FOREIGN PATENT DOCUMENTS

WO    WO 2008/061537 A2    5/2008
WO    WO 2010/120508 A2    10/2010

OTHER PUBLICATIONS

Nikiforov et al. (PCR Methods and Applications, 1994, vol. 3: 285-291).*
Najafi-Shoushtari et al., "MicroRNA-33 and the SREBP Host Genes Cooperate to Control Cholesterol Homeostasis", *Sceincexpress*, 2010, pp. 1-4.
Patrick et al., "Defective erythroid differentiation in miR-451 mutant mice mediated by 14-3-3ξ", *Genes & Development*, vol. 24, 2010, pp. 1614-1619.
Rayner et al., "miR-33 Contributes to the Regulation of Cholesterol Homeostasis", *Sciencexpress*, 2010, pp. 1-4.
Trajkovski et al., "MicroRNAs 103 and 107 regulate insulin sensitivity", *Nature*, vol. 000, 2011, pp. 1-6.
Yu et al., "miR-451 protects against erythroid oxidant stress by repressing 14-3-3ξ", *Genes & Development*, vol. 24, 2010, pp. 1620-1633.
Supplemental European Search Report dated Jul. 16, 2014 for European Patent Application No. 11 84 2512.
T. J. Marquart et al: "miR-33 links SREBP-2 induction to repression of sterol transporters", Proceedings of The National Academy of Sciences, vol. 107, No. 27, Jul. 6, 2010, pp. 12228-12232, XP055011036, ISSN: 0027-8424.

* cited by examiner

*Primary Examiner* — Kimberly Chong
(74) *Attorney, Agent, or Firm* — Merchant & Gould P.C.

(57) ABSTRACT

The present invention relates to oligonucleotides for modulation of target RNA activity. Thus, the invention provides oligonucleotides that bind to microRNA binding sites of target RNA. The oligonucleotides may activate RNase H or RNAi. In a preferred embodiment, the oligonucleotides prevents a micro RNA from binding to its binding site of the target RNA and thereby prevent the microRNA from regulating the target RNA. Such oligonucleotides have uses in research and development of new therapeutics.

6 Claims, No Drawings

OLIGONUCLEOTIDES FOR MODULATION OF TARGET RNA ACTIVITY

This application is a National Stage Application of PCT/DK2011/050447, filed 23 Nov. 2011, which claims benefit of Serial No. PA 2010 01061, filed 23 Nov. 2010 in Denmark and which applications are incorporated herein by reference. To the extent appropriate, a claim of priority is made to each of the above disclosed applications.

BACKGROUND OF THE INVENTION

The present invention relates to oligonucleotides that can be used to affect the activity of target RNAs.

The first generation of such oligonucleotides were antisense oligonucleotides that were intended to affect the activity of target mRNAs. One reason for interest in such oligonucleotides is the potential for exquisite and predictable specificity that can be achieved because of specific base pairing. In other words, it is in theory very simple to design an oligonucleotide that is highly specific for a given nucleic acid, such as an mRNA.

However, it has turned out simple base pairing is often not enough to achieve regulation of a given target mRNA, i.e. an oligonucleotide complementary to a given target mRNA does not necessarily affect the activity of the target mRNA. If the oligonucleotide targets the open reading frame of an mRNA, it may e.g. be that the translational apparatus simply displaces the oligonucleotide during translation. Therefore, means where developed that would improve the regulatory activity of the oligonucleotide.

E.g. oligonucleotides that can activate RNase H cleavage of the target mRNA were developed. One potential disadvantage of such oligonucleotides is that they may mediate cleavage of other RNAs than the intended target mRNA, i.e. giving rise to off-target effects. Still, such oligonucleotides acting through RNase H cleavage are in clinical trials for treatment of various diseases.

Recently, research has shown that eukaryotic cells, including mammalian cells, comprise a complex gene regulatory system (herein also termed RNAi machinery) that uses RNA as specificity determinants. This system can be triggered by so called siRNAs that may be introduced into a cell of interest to regulate the activity of a target mRNA. Currently, massive efforts go into triggering the RNAi machinery with siRNAs for specific regulation of target RNAs, in particular target mRNAs. This approach is widely regarded as having great promise for the development of new therapeutics. As will also be outlined below, a major advantage of this approach is that specificity of the siRNA lies in the degree of complementarity between the guide strand of the siRNA and the target RNA, i.e. target specificity can be controlled. However, it has turned out that siRNAs may be less specific than initially thought. Initially, it was believed that only target RNAs that harboured stretches of complete complementarity to the guide strand of the siRNA would be affected, i.e. targeted by the RNAi machinery. New research indicates that siRNAs indeed do result in significant off-target effects, i.e. regulation of non-intended targets. It is now believed that these off-targets stem from the siRNAs, or rather the guide strand of the siRNAs, acting as microRNAs.

MicroRNAs are a class of endogenous RNA molecules that has recently been discovered and that, as siRNA, function via the RNAi machinery. Currently, about 500 human microRNAs have been discovered and the number is rapidly increasing. It is now believed that more than one third of all human genes may be regulated by microRNAs. Therefore, microRNAs themselves may be used to regulate the activity of target RNAs, and consequently e.g. be used as therapeutics.

However, microRNAs generally act at more than one target RNA, i.e. they are promiscuous. Thus, introduction of a microRNA into the cell or regulating the level of a microRNA will affect the activity of more than one target mRNA and consequently often give rise to undesired off-target effects or unintended effects.

A recent approach has been put forward, wherein the activity of a target RNA is regulated by inhibiting the activity of a microRNA. The microRNA can be inhibited using complementary oligonucleotides that have been termed antimirs and antagomirs. Since the microRNA is itself promiscuous, the antimir or antagomir will affect the activity of more than one target RNA.

SUMMARY OF THE INVENTION

The present invention relates to oligonucleotides for modulating the activity of a target RNA. The oligonucleotides of the invention may activate RNase H, RNAi or prevent RNAi. In a preferred embodiment, oligonucleotides of the invention are capable of preventing a microRNA from regulating a target RNA.

Thus, a first aspect of the invention is an oligonucleotide comprising a contiguous sequence complementary to at least 8 contiguous bases of any of SEQ ID NO: 1-17 or any of SEQ ID NO: 1-17 comprising 1, 2 or 3 substitutions.

Other aspects of the invention relates to a method of modulating the activity of a target RNA, a pharmaceutical composition comprising an effective amount of the oligonucleotide of the invention, the oligonucleotide of the invention for use as medicine and a method of treatment comprising administering a therapeutically effective amount of the oligonucleotide of the invention to a person in need thereof.

DETAILED DESCRIPTION OF THE INVENTION

Definitions

The terms "regulate" and "modulate" are used interchangeably herein.

When referring to the "activity of a target mRNA", what is typically meant is the expression of the target mRNA, i.e. translation into a protein or peptide. Thus, regulation of the activity of a target mRNA may include degradation of the mRNA and/or translational regulation. Regulation may also include affecting intracellular transport of the mRNA. In a preferred embodiment of the invention, the oligonucleotide is capable of regulating the expression of the target mRNA. In another preferred embodiment, the oligonucleotide may mediate degradation of the target mRNA. The activity may also be replication.

When the target RNA is a viral RNA, the oligonucleotide of the invention may affect replication of the virus or otherwise interfere with the proliferation of the virus.

As used herein, regulation may be either positive or negative. I.e. a regulator (e.g. oligonucleotide or microRNA) may increase the activity of the target (e.g. target mRNA) or it may decrease the activity of the target.

When referring to the "target sequence of an RNA", what is meant is the region of the RNA involved in or necessary for microRNA regulation. The terms target region and target sequence are used interchangeably herein.

Not intended to be bound by theory, it is believed that this region comprise bases that interact directly with the microRNA during microRNA regulation of the target RNA.

In a preferred embodiment, the target sequence is the region of the target RNA necessary for microRNA regulation. Such region may be defined using a reporter system, wherein systematic deletions of the target RNA are tested for activity to define the target sequence. As will be clear from the specification, also oligonucleotides of the invention may be used to define the region of the target RNA necessary for microRNA regulation. Preferably, the target sequence comprises an antiseed sequence, which is complementary to the seed sequence of a microRNA and also complementary to a guide sequence of an oligonucleotide of the invention.

The term microRNA as used herein has the same meaning as typically in the art. I.e. the term microRNA refers to a small non-translated RNA of typically 18-22 nucleotides that is capable of regulating the activity of a target mRNA. A microRNA is typically processed from pri-microRNA to short stem-loop structures called pre-microRNA and finally to mature miRNA. Both strands of the stem of the pre-microRNA may be processed to a mature microRNA.

The miRBase (http://microrna.sanger.ac.uk/sequences/) is a compilation of known microRNAs. Also predicted and known targets of the microRNAs can be found on this site.

The term siRNA (short interfering RNA) as used herein has the same meaning as typically in the art. I.e. the term siRNA refers to double stranded RNA complex wherein the strands are typically 18-22 nucleotides in length. Very often, the complex has 3'-overhangs.

When referring to the RNAi machinery herein, what is meant are the cellular components necessary for the activity of siRNAs and microRNAs or for the RNAi pathway. A major player of the RNAi machinery is the RNA induced silencing complex (the RISC complex).

As referred to herein, an RNA unit is one of the monomers that make up an RNA polymer. Thus, an RNA unit is also referred to as an RNA monomer or a RNA nucleotide. Likewise, a DNA unit is one of the monomers that make up a DNA polymer and a DNA unit may also be referred to as a DNA monomer or a DNA nucleotide.

When referring to a base, what is meant is the base of a nucleotide. The base may be part of DNA, RNA, INA, LNA or any other nucleic acid or nucleic acid capable of specific base pairing. The base may also be part of PNA (peptide nucleic acid) or morpholino. In some embodiments, the base may be a universal base.

When referring the length of a sequence, reference may be made to the number of units or to the number of bases.

When referring to a complementary sequence, G pairs to C, A pairs to T and U and vice versa. In a preferred embodiment, G also pairs to U and vice versa to form a so-called wobble base pair. In another preferred embodiment, the base inosine (I) may be comprised within either in a microRNA or oligonucleotide of the invention. I base pairs to A, C and U. In still another preferred embodiment, universal bases may be used. Universal bases can typically basepair to G, C, A, U and T. Often universal bases do not form hydrogen bonds with the opposing base on the other strand. In still another preferred embodiment, a complementary sequence refers to a contiguous sequence exclusively of Watson-Crick base pairs.

As used herein, the term "capable of base pairing with" is used interchangeably with "complementary to".

First Aspect

In a first aspect, the present invention provides an oligonucleotide comprising a contiguous sequence complementary to at least 8 contiguous bases of any of SEQ ID NO: 1-17 or any of SEQ ID NO: 1-17 comprising 1, 2 or 3 substitutions. When referring to a substitution herein, it means that the base at a particular position may have been substituted for another base. The substitution may be because of the presence of a single nucleotide polymorphism in the target RNA. In one embodiment, the term substitution also covers deletions and additions. More preferably, the term substitution does not cover deletions and additions.

SEQ ID NO: 1-17 represents sequences of verified microRNA targets (also termed target RNAs) or putative microRNA targets. Therefore, oligonucleotides of the invention can be used to verify whether SEQ ID NO: 1-17 do indeed comprise a microRNA target and is subject to microRNA regulation. Moreover, the oligonucleotides of the invention may also be used to modulate the activity of the target RNA, e.g. to study regulatory networks in basic research or to up or down regulate the target RNA.

The oligonucleotides of the invention may also find therapeutic application, e.g. when a particular microRNA is upregulated and cause unwanted microRNA regulation of a target RNA. Another situation is when the presence of a SNP (single nucleotide polymorphism) gives rise to a microRNA target and hence cause unwanted microRNA regulation. There may also be situations where neither microRNA nor mRNA is dysregulated, but where preventing their interaction still leads to a desirable outcome, e.g. increased HDL in blood or increased insulin sensitivity, see examples section.

TABLE 1

List of target sequences. More sequences are given in the examples section.

| SEQ ID NO | GENE | SEQUENCE |
|---|---|---|
| 1 | ABCA1-1 | CUAUUCAAUGCAAUGCAAUUCAAUGCAAUGAAAACAAAAU |
| 2 | ABCA1-2 | UGUACUGAUACUAUUCAAUGCAAUGCAAUUCAAUGCAAUG |
| 3 | ABCA1-3 | GAUACUGUACUGAUACUAUUCAAUGCAAUGCAAUUCAAUG |
| 4 | YWHAZ | UUACUCUGGAUAAGGGCAGAAACGGUUCACAUUCCAUUAU |
| 5 | cav1-1 | AGCACUUGCAACCGUCUGUUAUGCUGUGACACAUGGCCCC |
| 6 | cav1-2 | AUUGUGUGAGCCUAUCAGAGUUGCUGCAAACCUGACCCCU |

Contiguous Complementary Sequences

In another embodiment, the oligonucleotide of the invention comprises or consist of a contiguous sequence complementary to a sequence selected from the group consisting of at least 9 contiguous bases, at least 10 contiguous bases, at least 11 contiguous bases, at least 12 contiguous bases, at least 13 contiguous bases, at least 14 contiguous bases, at least 15 contiguous bases, at least 16 contiguous bases, at least 17 contiguous bases, at least 18 contiguous bases, at least 19 contiguous bases, at least 20 contiguous bases, at least 22 contiguous bases, at least 25 contiguous bases, at least 30 contiguous bases, and at least 35 contiguous bases of any of SEQ ID NO: 1-17 or any of SEQ ID NO: 1-17 comprising 1, 2 or 3 substitutions.

In yet another embodiment, the oligonucleotide of the invention comprises or consists of a contiguous sequence complementary to a sequence selected from the group consisting of no more than 8 contiguous bases, no more than 9 contiguous bases, no more than 10 contiguous bases, no more than 11 contiguous bases, no more than 12 contiguous bases, no more than 13 contiguous bases, no more than 14 contiguous bases, no more than 15 contiguous bases, no more than 16 contiguous bases, no more than 17 contiguous bases, no more than 18 contiguous bases, no more than 19 contiguous bases, no more than 20 contiguous bases, no more than 22 contiguous bases, no more than 25 contiguous bases, no more than 30 contiguous bases, and no more than 35 contiguous bases of any of SEQ ID NO: 1-17 or any of SEQ ID NO: 1-17 comprising 1, 2 or 3 substitutions.

In another embodiment, the oligonucleotide of the invention comprises or consists of a contiguous sequence complementary to a sequence selected from the group consisting of 8 contiguous bases, 9 contiguous bases, 10 contiguous bases, 11 contiguous bases, 12 contiguous bases, 13 contiguous bases, 14 contiguous bases, 15 contiguous bases, 16 contiguous bases, 17 contiguous bases, 18 contiguous bases, 19 contiguous bases, 20 contiguous bases, 21 contiguous bases, 22 contiguous bases, 23 contiguous bases, 24 contiguous bases, 25 contiguous bases, 30 contiguous bases, and 35 contiguous bases of any of SEQ ID NO: 1-17 or any of SEQ ID NO: 1-17 comprising 1, 2 or 3 substitutions.

Even more preferably, oligonucleotide of the invention comprises or consists of a contiguous sequence selected from the group consisting of 8-25 bases, 10-22 bases and 12-20 bases complementary to any of SEQ ID NO: 1-17 or any of SEQ ID NO: 1-17 comprising 1, 2 or 3 substitutions.

Thus, contiguous base pairs can be formed between the oligonucleotide of the invention and any of SEQ ID NO: 1-17 or any of SEQ ID NO: 1-17 comprising 1, 2 or 3 substitutions.

Particular preferred sequences are those of table 1, i.e. SEQ ID NO: 1-6.

Preferably, consecutive base pairing includes positions 22-27 of any of SEQ ID NO: 1-6 or any of SEQ ID NO: 1-6 comprising 1, 2 or 3 substitutions. I.e. preferably, the oligonucleotide of the invention comprise a contiguous sequence complementary to position 22-27 of SEQ ID NO: 1-6 or any of SEQ ID NO: 1-6 comprising 1, 2 or 3 substitutions.

Consecutive base pairing covering position 22-27 is important because this region corresponds to the seed region of a microRNA.

In one embodiment, base pairing ends at position 27. In other embodiments, base pairing ends respectively at position 28, 29, 30, 31, 32, 33, 34, 35, 36, 37, 38, 39 and 40.

In another embodiment, base pairing starts at position 22. In other embodiments, base pairing starts respectively at position 21, 20, 19, 18, 17, 16, 15, 14, 13, 12, 11, 10, 9, 8, 7, 6, 5, 4, 3, 2 and 1.

In still another embodiment, base pairing includes positions 8-28, 8-27, 9-27, 10-27, 11-27, 12-27, 13-27, 14-27, 15-27, 16-27, 17-27, 18-27, 19-27, 20-27, 21-27, 9-28, 10-28, 11-28, 12-28, 13-28, 14-28, 15-28, 16-28, 17-28, 18-28, 19-28, 20-28 and 21-28.

Length of Oligonucleotide

As is also outlined in the examples section, the oligonucleotides can be adjusted in length to fulfil various criteria. For strong binding to its target RNA, the length may be increased. In some cases, delivery into cells may be improved may using shorter oligonucleotides. Further, in other cases, the position of the oligonucleotide respectively to the antiseed sequence of the target RNA may be adjusted, i.e. the position of bases complementary to position 22-27 of the target RNAs of table 1 (SEQ ID NO: 1-6) may be adjusted such that they are placed e.g. at the 5'end of oligonucleotide, at the 3'end or in the middle of the oligonucleotide. Preferably, the position of bases complementary to position 22-27 are placed in the oligonucleotide such that they start at position 1, position 2, position 3, position 4, position 5 or position 6, or at a position upstream of position 2, position 3, position 4, position 5 or position 6 or at a position downstream of position 1, position 2, position 3, position 4, position 5 or position 6, wherein the positions are counted from the 5'end of the oligonucleotide Preferably, the oligonucleotides of the invention are between 8 and 25 bases in lengths. Even more preferably, the oligonucleotides of the invention are between 10 and 20 bases in length or between 12 and 22 bases. Preferably, the oligonucleotide is complementary to the target RNAs of table 1 (SEQ ID NO: 1-6) over its entire length and likewise for SEQ ID NO: 7-17.

Substitutions

In one embodiment, any of SEQ ID NO: 1-17 may only comprise 1 or 2 substitutions.

In yet another one embodiment, any of SEQ ID NO:1-17 may only comprise only 1 substitution.

In a further embodiment, any of SEQ ID NO: 1-17 may not comprise any substitutions.

In yet another embodiment, the substitutions of any of SEQ ID NO: 1-17 are located in the region of complementarity between the oligonucleotide of the invention and any of SEQ ID NO: 1-17.

Substitutions may be present in any of SEQ ID NO: 1-17 for various reasons. They may e.g. be SNPs that may enhance or decrease microRNA regulation of the given target RNA. An SNP may even create a new micro RNA target site such as to cause aberrant microRNA regulation of the given target RNA. Also RNA editing may give rise to substitutions.

In still another embodiment, only 1 substitution may be present in position 22-27 of any of SEQ ID NO: 1-6. In this embodiment, further substitutions may be present elsewhere in the target sequence. Thus, there may e.g. be one substitution in position 22-27 and one or two more substitutions elsewhere in the target RNA (any of SEQ ID NO: 1-6).

Activity of the Oligonucleotides of the Invention

RNase H Activation

In one embodiment of the invention, the oligonucleotide is capable of activating RNase H. RNase H will cleave the RNA part of a RNA-DNA duplex and the structural requirements for RNase H activation are well-known to the skilled man. This mechanism is very often used to achieve traditional antisense regulation e.g. by employing so-called gapmers. Gapmers are antisense oligonucleotides that comprise a central region with deoxy sugars (the gap) and modified flanks. Gapmers very often comprises phosphorothioate internucleotide linkages to improve biostability and the flanks comprise e.g. 2-O-modifications that also improve biostability, i.e. resistance against nucleolytic attack. The flanks may also comprise modifications that increase the melting temperature of the gapmer base paired to a complementary nucleic acid. Some 2-O-modifications (e.g. 2-O-Methyl and LNA) at the flanks are capable of both improving biostability and increasing the melting temperature of the gapmer base paired to a complementary nucleic acid.

Thus, in one preferred embodiment, the oligonucleotide of the invention comprises a contiguous sequence of deoxynucleotides of at least 5 units to enable RNase H activation and hence cleavage of the target RNA. Even more preferably, 6, 7, or 8 contiguous deoxynucleotides should be present.

In another embodiment, the oligonucleotide of the invention is not capable of activating RNase H. In this embodiment, the oligonucleotide does not comprise a contiguous sequence of unmodified DNA that exceeds a length selected from the group consisting of: 3 bases, 4 bases, 5 bases, 6 bases, 7 bases, 8 bases, 9 bases, 10 bases and 11 bases. Most preferably, the stretch of unmodified DNA does not exceed 3 bases. The skilled man will easily be able to test whether a given oligonucleotide does indeed activate RNase H. One kind of oligonucleotides well known to the skilled man that does not recruit RNase H is so-called steric block oligonucleotides.

RNAi Activation

The RNAi machinery is a sophisticated gene regulatory system that is guided by RNA. Thus, microRNAs guide the RNAi machinery to target mRNAs (or other target RNAs such as viral target RNAs) to affect the activity of the target mRNA. The RNAi machinery may affect translation of the mRNA directly or it may affect the stability of the target mRNA, i.e. mediate direct degradation of the target mRNA. Not intended to be bound by theory, it is believed that the degree of complementarity between microRNA and target mRNA is a key element as to whether the target mRNA is subjected to translational regulation or degradation.

Endogenous microRNAs are processed from precursor stem-loops and incorporated into a so called RNA induced silencing complex (RISC complex). The details of this process are still poorly understood.

The cellular RNAi machinery has been extensively used to affect the activity of cellular mRNAs by introducing synthetic double stranded RNA complexes termed siRNAs into the cell. As mentioned above, siRNAs are short double stranded RNA complexes comprising a passenger strand and a complementary guide strand. The guide strand of siRNA is incorporated into the RISC complex, where after the RISC complex can affect the activity of mRNA harbouring complementary sequences to the guide strand. Thus, siRNAs are a class of compounds that is thought to be capable of efficiently and specifically targeting any mRNA and consequently, siRNAs are regarded potentially as a new class of therapeutics.

A common feature of siRNAs and microRNAs is that they recruit the cellular RNAi machinery to affect the activity of target RNAs.

In one embodiment, the oligonucleotides of the invention are capable of recruiting the RNAi machinery and directing the RNAi machinery to the target RNA. This may result in cleavage of the target RNA or translational repression of the target RNA. In this embodiment, the oligonucleotide may be a siRNA. I.e. the oligonucleotide is hybridised to a complementary oligonucleotide, typically over a length of 20-22 bases and very often with 3'overhangs of 1-3 bases. The oligonucleotide may also act as a microRNA, without being identical to a naturally occurring microRNA. Where naturally occurring microRNAs typically regulates many target RNAs, a oligonucleotide of the invention acting as a microRNA may be designed to only regulate a few target RNAs or only one target RNA. Gene specific oligonucleotides of the invention functioning as a microRNA may e.g. be capable of base pairing to position 22-28 of any of SEQ ID NO: 1-6 and e.g. also to position 7-16 or position 7-18.

Oligonucleotides of the invention designed for RNase H activation or for RNAi activation will be more potent than an average oligonucleotide designed for RNaseH activation or RNAi activation, because they target a microRNA target site, which has evolved for interaction via an antisense mechanism and is consequently more accessible than average sites.

In another embodiment, the oligonucleotides of the invention cannot recruit the RNAi machinery. This can easily be achieved by using a single stranded oligonucleotide that is modified e.g. with LNA at every second or third position. One kind of oligonucleotides well known to the skilled man that does not recruit RNase H is so-called steric block oligonucleotides.

Blockmir

In another embodiment, the oligonucleotides of the invention cannot recruit the RNAi machinery and as will clear also not recruit RNase H. In this embodiment, it is preferred that the oligonucleotides of the invention are capable of blocking the activity of the RNAi machinery at a particular target RNA. The oligonucleotides may do so by sequestering the target sequence (micro RNA binding site) of the target RNA, such that the RNAi machinery will not recognize the target sequence, as it is base paired to an oligonucleotide of the invention. Oligonucleotides of the invention with this activity may also be referred to as blockmirs, because they block the regulatory activity of a given microRNA at a particular target RNA. Blockmirs may be viewed as steric block oligonucleotides directed to microRNA binding sites.

Thus, in a preferred embodiment, the oligonucleotide is capable of blocking the regulatory activity of a microRNA at a particular target RNA. Preferably, the microRNA is an endogenous microRNA.

If the microRNA is a positive regulator of the target RNA, the oligonucleotide will be a negative regulator of the target RNA.

Most often, the microRNA is a negative regulator of the target RNA. Thus, in another embodiment, the oligonucleotide is a positive regulator of the target RNA and thus enhances the activity of the target RNA. This is contrary to traditional antisense oligonucleotides, microRNAs and siRNAs that typically act as negative regulators by mediating translational repression and/or degradation of the targetRNA.

Off-Target Effects

In most embodiments, off-target binding of the blockmir will have very few or no effects. This is contrary to antimirs, RNAi mediated by siRNAs and microRNAs, and RNase H mediated antisense regulation, which may all give rise to off-target effects or unintended effects. The blockmir only has an effect if it binds to its intended target, i.e. a microRNA target region and thereby prevents microRNA regulation of the target RNA.

Thus, in a preferred embodiment, the blockmir will have reduced off-target effects or unintended effects, as compared to regulating the activity of the target mRNA using an antimir.

An antimir, as used in the present context, is an oligonucleotide that can base pair with a microRNA and thereby inhibit the activity of the microRNA. Since most microRNAs are promiscuous, i.e. they regulate more than one target, regulation of a particular microRNA will affect the activity of more than one target mRNA. Thus, when it is desired to only regulate the activity of one particular target mRNA, regulation of other target mRNAs may be referred to as off-target effects of the antimir. Such effects could also be referred to as unintended effects or side effects of the antimir.

Using a microRNA to affect or regulate the activity of a target mRNA, instead of an antimir will obviously also have off-target effects or unintended effects.

In conclusion, blockmirs of the present invention are characteristic in that they affect the activity of a target RNA by preventing microRNA regulation of the target RNA. Thus, blockmirs of the present invention will have reduced off target effects as compared to both traditional antisense oligonucleotides, antimirs, and RNAi mediated regulation using microRNAs and siRNAs.

Architecture and Chemistry

The activity of the oligonucleotide of the invention can be affected and controlled by architecture and chemistry.

Thus, different modifications may be placed at different positions to prevent the oligonucleotide from activating RNase H and/or being capable of recruiting the RNAi machinery. In another embodiment, they may be placed such as to allow RNase H activation and/or recruitment of the RNAi machinery.

As referred to herein, any non-natural nucleotides are referred to as modifications of the oligonucleotide. The modifications may be non-natural bases, e.g. universal bases. It may be modifications on the backbone sugar or phosphate, e.g. 2'-O-modifications including LNA or phosphorothioate linkages. As used herein, it makes no difference whether the modifications are present on the nucleotide before incorporation into the oligonucleotide or whether the oligonucleotide is modified after synthesis.

Preferred modifications are those that increase the affinity of the oligonucleotide for complementary sequences, i.e. increases the tm (melting temperature) of the oligonucleotide base paired to a complementary sequence.

Such modifications include 2'-O-Flouro, 2'-O-methyl, 2'-O-methoxyethyl. Also the use of LNA (locked nucleic acid) units, phosphoramidate, PNA (peptide nucleic acid) units or INA (intercalating nucleic acid) units is preferred. For shorter oligonucleotides, it is preferred that a higher percentage of affinity increasing modifications are present. If the oligonucleotide is less than 12 or 10 units long, it may be composed entirely of LNA units.

Preferred are also modifications that increase the biostability of the oligonucleotide, which also includes 2'-O-Flouro, 2'-O-methyl, 2'-O-methoxyethyl. Also the use of LNA (locked nucleic acid) units, PNA (peptide nucleic acid) units, phosphoramidate units, or INA (intercalating nucleic acid) units is preferred. A wide range of other non-natural units may also be build into the oligonucleotide. E.g. morpholino, 2'-Deoxy-2'-fluoro-arabinonucleic acid (FANA) and arabinonucleic acid (ANA).

In a preferred embodiment, the fraction of units modified at either the base or sugar relatively to the units not modified at either the base or sugar is selected from the group consisting of less than less than 99%, 95%, less than 90%, less than 85% or less than 75%, less than 70%, less than 65%, less than 60%, less than 50%, less than 45%, less than 40%, less than 35%, less than 30%, less than 25%, less than 20%, less than 15%, less than 10%, and less than 5%, less than 1%, more than 99%, more than 95%, more than 90%, more than 85% or more than 75%, more than 70%, more than 65%, more than 60%, more than 50%, more than 45%, more than 40%, more than 35%, more than 30%, more than 25%, more than 20%, more than 15%, more than 10%, and more than 5% and more than 1%.

Lipids and/or peptides may also be conjugated to the oligonucleotide. Such conjugation may both improve bioavailability and prevent the oligonucleotide from activating RNase H and/or recruiting the RNAi machinery. Conjugation of larger bulkier moieties is preferably done at the central part of the oligonucleotide, e.g. at any of the most central 5 units. Alternatively, at one of the bases complementary to one of position 22-27 of any of SEQ ID NO: 1-6. In yet another embodiment, the moiety may be conjugated at the 5'end or the 3'end of the oligonucleotide.

A preferred hydrophobic moiety is cholesterol moiety that may be conjugated to the oligonucleotide and prevent the oligonucleotide from recruiting the RNAi machinery and improve the bioavailability of the oligonucleotide. The cholesterol moiety may be conjugated to at one of the bases complementary to one of position 22-27 of any of SEQ ID NO: 1-6, at the 3'end or the 5'end of the oligonucleotide.

Further, in a preferred embodiment, phosphorothioate internucleotide linkages may connect the units to improve the biostability of the oligonucleotide. All linkages of the oligonucleotide may be phosphorothioate linkages. In another embodiment, the fraction of phosphorothioate linkages is selected from the group consisting of less than 95%, less than 90%, less than 85% or less than 75%, less than 70%, less than 65%, less than 60%, less than 50%, more than 95%, more than 90%, more than 85% or more than 75%, more than 70%, more than 65%, more than 60% and more than 50%.

In yet another embodiment, the oligonucleotide may comprise a mix of DNA units and RNA units such as to prevent the oligonucleotide from activating RNase H and to at the same time prevent the oligonucleotide from recruiting the RNAi machinery. E.g. a DNA unit may be followed by a RNA unit that is again followed by a DNA unit and so on. The DNA units and RNA units may come in blocks. The blocks may have a length of 2 units, 3 units, 4 units, 5 units or 6 units and blocks of different length may be comprised with the same oligonucleotide.

In another preferred embodiment, the oligonucleotide comprises a mix of LNA units and RNA units with a 2'-O-methyl. Such LNA/2'O-Methyl mixmers have been used as steric block inhibitors of Human Immunodeficiency Virus Type 1 Tat-Dependent Trans-Activation and HIV-1 Infectivity.

LNA-DNA

In one embodiment, the oligonucleotide of the invention does not comprise any RNA units. Few or no RNA units may be used to prevent the oligonucleotide from being capable of recruiting the RNAi machinery. As outlined above, chemical modifications/non-natural units can do the same. One such example is an oligonucleotide comprising LNA units and DNA units. In a preferred embodiment, the oligonucleotide comprises exclusively LNA units and DNA and these may be connected by phosphorothioate linkages as outlined above.

In another embodiment, the oligonucleotide of the invention does not comprise any DNA units.

In still another embodiment, the oligonucleotide of the invention does not comprise any morpholino units and/or LNA units.

In a preferred embodiment, the oligonucleotides comprise a number of nucleotide units that increase the affinity for complementary sequences selected from the group of: at least 1 units, at least 2 units, at least 3 units, at least 4 units, at least 5 units, at least 6 units, at least 7 units, at least 8 units, at least 9 units, at least 10 units, at least 11 units, at least 12 units, at least 13 units, at least 14 units, at least 15 units, at least 16 units, at least 17 units, at least 18 units, at least 19 units, at least 20 units, at least 21 units, and at least 22 units.

In another preferred embodiment, the oligonucleotides comprise a number of nucleotide units that increase the affinity for complementary sequences selected from the group of: no more than 1 units, no more than 2 units, no more than 3 units, no more than 4 units, no more than 5 units, no more than 6 units, no more than 7 units, no more than 8 units, no more than 9 units, no more than 10 units, no more than 11 units, no more than 12 units, no more than 13 units, no more than 14 units, no more than 15 units, no more than 16 units, no more than 17 units, no more than 18 units, no more than 19 units, no more than 20 units, no more than 21 units, and no more than 22 units.

In a yet another preferred embodiment, the oligonucleotides comprise a number of nucleotide units that increase the affinity for complementary sequences selected from the group of: 1 units, 2 units, 3 units, 4 units, 5 units, 6 units, 7 units, 8 units, 9 units, 10 units, 11 units, 12 units, 13 units, 14 units, 15 units, 16 units, 17 units, 18 units, 19 units, 20 units, 21 units, and 22 units.

In a preferred embodiment, nucleotide units that increase the affinity for complementary sequences are located at the flanks of the oligonucleotide. E.g. if the oligonucleotide comprise e.g. 10 LNA units, 5 may be located at the 5'end and the other 5 units may be located at the 3'end. In another embodiment, the nucleotide units that increase the affinity for complementary sequences are at the central portion of the oligonucleotide. Thus, if the oligonucleotide has a length of 18 units of which 8 are LNA units, 5 natural units may be followed by 8 LNA units again followed by 5 natural units.

The nucleotide units that increase the affinity for complementary sequences may also be distributed evenly over the length of the oligonucleotide. E.g. at every 2, 3, 4, 5, 6 positions or any combinations thereof.

Single-Stranded Vs. Double Stranded

The oligonucleotide of the invention is preferably not base paired with a complementary oligonucleotide or intended for use a base paired with a complementary oligonucleotide. I.e. it should be single stranded to facilitate interaction with a target RNA and in certain embodiments, also to prevent recruitment of the RNAi machinery.

In another embodiment, the oligonucleotide is base paired to a complementary oligonucleotide. This may e.g. be the case when the oligonucleotide is acting as a siRNA or a microRNA and/or it may also be used to improve delivery of the oligonucleotide. Thus, in one embodiment, the oligonucleotide is base paired to a RNA molecule that is degraded by RNase H, when the oligonucleotide enters its target cell. In this way, the oligonucleotide is liberated on site.

A few exemplary architectures are given here:

XxxXxxXxxXxxXxxX

XxXxXxXxXxXxXxXxXxX

XxXxxXxXxxXxXxxX

XXXXXXXXXX wherein X denote a LNA unit and x denote either an RNA unit, DNA unit, 2'-O-methyl-RNA unit, or other 2'-O-modified unit.

xxxxxxxxxxxxxx wherein X denotes a 2'-O-methyl-RNA unit or other 2'-O-modified unit.

xxxxxxxxxxxxxxxxxxxxxxx wherein X denote a morpholino unit.

LNA is often used in combination with other units, because LNA has a very strong effect on the affinity of the oligonucleotide for complementary sequences. If the oligonucleotide is short, e.g. less than 12 or 10 units, it may be fully composed of LNA units.

Other units that have a less dramatic effect on affinity may be used 100%. I.e. an oligonucleotide of 20 units or more may be fully modified with 2'-O-methyl-RNA units or other 2'-O-modified units. The same applies e.g. to morpholino.

A plethora of modifications are available that will prevent the oligonucleotide from recruiting RNase H and the RNAi machinery. As mentioned earlier, steric block oligonucleotides are examples of oligonucleotides that do not recruit RNase h and the RNAi machinery and steric block oligonucleotides have been part of the state of the art for many years.

A second aspect of the invention is a method of modulating the activity of a target RNA comprising the steps of:
a. Providing a system comprising a target RNA
b. Introducing an oligonucleotide of the invention that targets the target RNA to the system
c. Thereby modulating the activity of the target RNA Preferably, the oligonucleotide prevents the activity of a microRNA at the target RNA and thereby regulates the activity of the target RNA.

In another embodiment, the oligonucleotide induces RNase H cleavage of the target RNA and thereby regulates the activity of the target RNA.

In yet another embodiment, the oligonucleotide induces RNAi degradation of the target RNA and thereby regulates the activity of the target RNA.

In a preferred embodiment of the second aspect of the invention, the system is either a cell extract or a cell In another preferred embodiment of the second aspect of the invention, the method is performed in vivo, ex vivo or in vitro.

Pharmaceutical Composition and Treatment

A third aspect of the invention is a pharmaceutical composition comprising the oligonucleotide of the invention. As the skilled man will understand from the above description, the oligonucleotide may be used for therapy in the same manner as siRNAs, microRNAs and antisense oligonucleotides, because they can be used to specifically affect the expression of a particular gene. Specific disease areas and conditions are described in the examples section.

A fourth aspect of the invention is a method of treatment comprising administering the oligonucleotide of the invention or the pharmaceutical composition of the invention to a person in need thereof.

A fifth aspect of the invention is the oligonucleotide of the invention for use as medicine.

A sixth aspect of the invention is use of the oligonucleotide of the invention for the preparation of a medicament for treatment of cancer, viral infection, immunological disease or cardiovascular disease.

A seventh aspect of the invention is use of the oligonucleotide for modulating the activity of a target RNA.

EXAMPLES

Example 1

Oligonucleotides for Increasing HDL

Two recent publications (Najafi-Shoushtari SH, Science. 2010 May 13. [Epub ahead of print]) (Rayner K J, Science. 2010 May 13. [Epub ahead of print]) suggest that microRNA-33 is a regulator of HDL-levels, such that overexpression of microRNA-33 decreases HDL and inactivation of microRNA-33 increases HDL. Thus, the Najafi-Shoushtari et al suggest "antisense therapeutic targeting of miR-33a/b as a novel strategy to increase HDL in individuals suffering from cardiometabolic diseases" and likewise Rayner et al suggest "antagonists of endogenous miR-33 may be a useful therapeutic strategy for enhancing ABCA1 expression and raising HDL levels in vivo."

Since microRNAs in general regulate a plethora of targets that may even differ in different organs and tissues, antagonizing microRNA-33 with an antisense oligonucleotide may entail a risk of unwanted side effects.

A more predictable approach with a reduced risk of unwanted side effects may be to block individual microRNA binding sites in target mRNA. Thus, as an alternative to the approaches suggested by the above cited for raising HDL levels in vivo, the present inventor suggest using so-called Blockmirs to block microRNA binding sites in ABCA1 mRNA, in particular microRNA-33 binding sites.

The 3'UTR of the ABCA1 mRNA comprise several microRNA-33 binding sites. In the following sequence, anti-seed sequences are shown in bold. Two sites are overlapping and a third site is located adjacent to the overlapping sites.

The 3'UTR of the ABCA1 mRNA (SEQ ID NO:7):

AGAAUCCUGUUCAUACGGGGUGGCUGAAAGUAAAGAGGAACUAGACUUUCCUUUGCACCA
UGUGAAGUGUUGUGGAGAAAAGAGCCAGAAGUUGAUGUGGGAAGAAGUAAACUGGAUACU
GUACUGAUACUAUUCAAUGCAAUGCAAUUCAAUGCAAUGAAAACAAAAUUCCAUUACAGG
GGCAGUGCCUUUGUAGCCUAUGUCUUGUAUGGCUCUCAAGUGAAAGACUUGAAUUUAGUU
UUUUACCUAUACCUAUGUGAAACUCUAUUAUGGAACCCAAUGGACAUAUGGGUUUGAACU
CACACUUUUUUUUUUUUUUUGUUCCUGUGUAUUCUCAUUGGGGUUGCAACAAUAAUUCA
UCAAGUAAUCAUGGCCAGCGAUUAUUGAUCAAAAUCAAAAGGUAAUGCACAUCCUCAUUC
ACUAAGCCAUGCCAUGCCCAGGAGACUGGUUUCCCGGUGACACAUCCAUUGCUGGCAAUG
AGUGUGCCAGAGUUAUUAGUGCCAAGUUUUUCAGAAAGUUUGAAGCACCAUGGUGUGUCA
UGCUCACUUUUGUGAAAGCUGCUCUGCUCAGAGUCUAUCAACAUUGAAUAUCAGUUGACA
GAAUGGUGCCAUGCGUGGCUAACAUCCUGCUUUGAUUCCCUCUGAUAAGCUGUUCUGGUG
GCAGUAACAUGCAACAAAAAUGUGGGUGUCUCCAGGCACGGGAAACUUGGUUCCAUUGUU
AUAUUGUCCUAUGCUUCGAGCCAUGGGCUACAGGGUCAUCCUUAUGAGACUCUUAAAUA
UACUUAGAUCCUGGUAAGAGGCAAAGAAUCAACAGCCAAACUGCUGGGGCUGCAAGCUGC
UGAAGCCAGGGCAUGGGAUUAAAGAGAUUGUGCGUUCAAACCUAGGGAAGCCUGUGCCCA
UUUGUCCUGACUGUCUGCUAACAUGGUACACUGCAUCUCAAGAUGUUUAUCUGACACAAG
UGUAUUAUUUCUGGCUUUUUGAAUUAAUCUAGAAAAUGAAAAGAUGGAGUUGUAUUUUGA
CAAAAAUGUUUGUACUUUUUAAUGUUAUUGGAAUUUUAAGUUCUAUCAGUGACUUCUGA
AUCCUUAGAAUGGCCUCUUUGUAGAACCCUGUGGUAUAGAGGGAGUAUGGCCACUGCCCCA
CUAUUUUUAUUUUCUUAUGUAAGUUUGCAUAUCAGUCAUGACUAGUGCCUAGAAAGCAAU
GUGAUGGUCAGGAUCUCAUGACAUUAUAUUUGAGUUUCUUUCAGAUCAUUUAGGAUACUC
UUAAUCUCACUUCAUCAAUCAAAUAUUUUUUGAGUGUAUGCUGUAGCUGAAAGAGUAUGU
ACGUACGUAUAAGACUAGAGAGAUAUUAAGUCUCAGUACACUUCCUGUGCCAUGUUAUUC
AGCUCACUGGUUUACAAAUAUAGGUUGUCUUGUGGGUUGUAGGAGCCCACUGUAACAAUAC
UGGGCAGCCUUUUUUUUUUUUUUUUAAUUGCAACAAUGCAAAAGCCAAGAAAGUAUAAG
GGUCACAAGUCUAAACAAUGAAUUCUUCAACAGGGAAAACAGCUAGCUUGAAAACUUGCU
GAAAAACACAACUUGUGUUUAUGGCAUUUAGUACCUUCAAAUAAUUGGCUUUGCAGAUAU
UGGAUACCCCAUUAAAUCUGACAGUCUCAAAUUUUUCAUCUCUUCAAUCACUAGUCAAGA
AAAAUAUAAAACAACAAAUACUUCCAUAUGGAGCAUUUUUCAGAGUUUUCUAACCCAGU
CUUAUUUUUCUAGUCAGUAAACAUUUGUAAAAAUACUGUUUCACUAAUACUUACUGUUAA
CUGUCUUGAGAGAAAAGAAAAAUAUGAGAGAACUAUUGUUUGGGGAAGUUCAAGUGAUCU
UUCAAUAUCAUUACUAACUUCUUCCACUUUUUCCAGAAUUUGAAUAUUAACGCUAAAGGU
GUAAGACUUCAGAUUUCAAAUUAAUCUUUCUAUAUUUUUUAAAUUUACAGAAUAUUAUAU
AACCCACUGCUGAAAAAGAAAAAAAUGAUUGUUUUAGAAGUUAAAGUCAAUAUUGAUUUU
AAAUAUAAGUAAUGAAGGCAUAUUUCCAAUAACUAGUGAUAUGGCAUCGUUGCAUUUUAC
AGUAUCUUCAAAAAUACAGAAUUUAUAGAAUAAUUUCUCCUCAUUUAAUAUUUUUCAAAA

-continued

UCAAAGUUAUGGUUUCCUCAUUUUACUAAAAUCGUAUUCUAAUUCUUCAUUAUAGUAAAU

CUAUGAGCAACUCCUUACUUCGGUUCCUCUGAUUUCAAGGCCAUAUUUUAAAAAAUCAAA

AGGCACUGUGAACUAUUUUGAAGAAAACACAACAUUUUAAUACAGAUUGAAAGGACCUCU

UCUGAAGCUAGAAACAAUCUAUAGUUAUACAUCUUCAUUAAUACUGUGUUACCUUUUAAA

AUAGUAAUUUUUUACAUUUUCCUGUGUAAACCUAAUUGUGGUAGAAAUUUUUACCAACUC

UAUACUCAAUCAAGCAAAAUUUCUGUAUAUUCCCUGUGGAAUGUACCUAUGUGAGUUUCA

GAAAUUCUCAAAAUACGUGUUCAAAAAUUUCUGCUUUUGCAUCUUUGGGACACCUCAGAA

AACUUAUUAACAACUGUGAAUAUGAGAAAUACAGAAGAAAAUAAUAAGCCCUCUAUACAU

AAAUGCCCAGCACAAUUCAUUGUUAAAAAACAACCAAACCUCACACUACUGUAUUUCAUU

AUCUGUACUGAAAGCAAAUGCUUUGUGACUAUUAAAUGUUGCACAUCAUUCAUUCACUGU

AUAGUAAUCAUUGACUAAAGCCAUUUGUCUGUGUUUUCUUCUUGUGGUUGUAUAUAUCAG

GUAAAAUAUUUUCCAAAGAGCCAUGUGUCAUGUAAUACUGAACCACUUUGAUAUUGAGAC

AUUAAUUUGUACCCUUGUUAUUAUCUACUAGUAAUAAUGUAAUACUGUAGAAAUAUUGCU

CUAAUUCUUUUCAAAAUUGUUGCAUCCCCCUUAGAAUGUUUCUAUUUCCAUAAGGAUUUA

GGUAUGCUAUUAUCCCUUCUUAUACCCUAAGAUGAAGCUGUUUUUGUGCUCUUUGUUCAU

CAUUGGCCCUCAUUCCAAGCACUUUACGCUGUCUGUAAUGGGAUCUAUUUUUGCACUGGA

AUAUCUGAGAAUUGCAAAACUAGACAAAAGUUUCACAACAGAUUUCUAAGUUAAAUCAUU

UUCAUUAAAAGGAAAAAAGAAAAAAAAUUUUGUAUGUCAAUAACUUUAUAUGAAGUAUUA

AAAUGCAUAUUUCUAUGUUGUAAUAUAAUGAGUCACAAAAUAAAGCUGUGACAGUUCUGU

UGGUCUACAGAA

Potential complexes are shown here with the microRNA (SEQ ID NO:18) shown below the mRNA sequence (SEQ ID NO:8):

```
UACUGAUACUAUUCAAUGCAAUGCAAUU-CAAUGCAAUGAAAACAAAAUUCCAUUACAGG
           ||||||||||||  |||||||
              ACGUUACGUUGAUGUUACGUG
```

```
UACUGAUACUAUUCAAUGCAAUGCAAUU-CAAUGCAAUGAAAACAAAAUUCCAUUACAGG
              | | |||||||||
           ACGUUACGUUGAUGUUACGUG
```

```
UACUGAUACUAUUCAAUGCAAUGCAAUU-CAAUGCAAUGAAAACAAAAUUCCAUUACAGG
                             |||||||
           ACGUUACGUUGAUGUUACGUG
```

Specific embodiments of the Blockmirs (directed to microRNA-33 binding sites) are described in the detailed description in particular with relation to SEQ NO:1-3.

Example 2

Oligonucleotides for Treatment of Hematopoietic Malignancies

Two recent papers (David M. Patrick, 2010) (Duonan Yu, 2010) described a role for microRNA-451 in erythropoiesis and suggested using antimirs directed to microRNA-451 for treatment of hematopoietic malignancies. An alternative approach may be to specifically prevent microRNA-451 from regulating one or more of its targets. One such target is 14-3ζ encoded by YWHAZ.

The 3'UTR of the YWHAZ mRNA (SEQ ID NO:9), with a microRNA-451 antiseed sequence indicated in bold:

```
CCGGCCUUCCAACUUUUGUCUGCCUCAUUCUAAAAUUUACACAGUAGACCAUUUGUCAUC
CAUGCUGUCCCACAAAUAGUUUUUUGUUUACGAUUUAUGACAGGUUUAUGUUACUUCUAU
UUGAAUUUCUAUAUUUCCCAUGUGGUUUUUAUGUUUAAUAUUAGGGGAGUAGAGCCAGUU
AACAUUUAGGGAGUUAUCUGUUUUCAUCUUGAGGUGGCCAAUAUGGGGAUGUGGAAUUUU
UAUACAAGUUAUAAGUGUUUGGCAUAGUACUUUUGGUACAUUGUGGCUUCAAAAGGGCCA
GUGUAAAACUGCUUCCAUGUCUAAGCAAAGAAAACUGCCUACAUACUGGUUUGUCCUGGC
GGGGAAUAAAAGGGAUCAUUGGUUCCAGUCACAGGUGUAGUAAUUGUGGGUACUUUAAGG
UUUGGAGCACUUACAAGGCUGUGGUAGAAUCAUACCCCAUGGAUACCACAUAUUAAACCA
UGUAUAUCUGUGGAAUACUCAAUGUGUACACCUUUGACUACAGCUGCAGAAGUGUUCCUU
UAGACAAAGUUGUGACCCAUUUUACUCUGGAUAAGGGCAGAAACGGUUCACAUUCCAUUA
UUUGUAAAGUUACCUGCUGUUAGCUUUCAUUAUUUUUGCUACACUCAUUUUAUUUGUAUU
UAAAUGUUUUAGGCAACCUAAGAACAAAUGUAAAAGUAAAGAUGCAGGAAAAAUGAAUUG
CUUGGUAUUCAUUACUUCAUGUAUAUCAAGCACAGCAGUAAAACAAAAACCCAUGUAUUU
AACUUUUUUUUAGGAUUUUUGCUUUUGUGAUUUUUUUUUUUUGAUACUUGCCUAACAUG
CAUGUGCUGUAAAAAUAGUUAACAGGGAAAUAACUUGAGAUGAUGGCUAGCUUUGUUUAA
UGUCUUAUGAAAUUUUCAUGAACAAUCCAAGCAUAAUUGUUAAGAACACGUGUAUUAAAU
UCAUGUAAGUGGAAUAAAAGUUUUAUGAAUGGACUUUUCAACUACUUUCUCUACAGCUUU
UCAUGUAAAUUAGUCUUGGUUCUGAAACUUCUCUAAAGGAAAUUGUACAUUUUUUGAAAU
UUAUUCCUUAUUCCCUCUUGGCAGCUAAUGGGCUCUUACCAAGUUUAAACACAAAAUUUA
UCAUAACAAAAAUACUACUAAUAUAACUACUGUUUCCAUGUCCCAUGAUCCCCUCUCUUC
CUCCCCACCCUGAAAAAAAUGAGUUCCUAUUUUUUCUGGGAGAGGGGGGAUUGAUUAGA
AAAAAAUGUAGUGUGUUCCAUUUAAAAUUUUGGCAUAUGGCAUUUUCUAACUUAGGAAGC
CACAAUGUUCUUGGCCCAUCAUGACAUUGGGUAGCAUUAACUGUAAGUUUUGUGCUUCCA
AAUCACUUUUUGGUUUUUAAGAAUUUCUUGAUACUCUUAUAGCCUGCCUUCAAUUUUGAU
CCUUUAUUCUUUCUAUUUGUCAGGUGCACAAGAUUACCUUCCUGUUUUAGCCUUCUGUCU
UGUCACCAACCAUUCUUACUUGGUGGCCAUGUACUUGGAAAAAGGCCGCAUGAUCUUUCU
GGCUCCACUCAGUGUCUAAGGCACCCUGCUUCCUUUGCUUGCAUCCCACAGACUAUUUCC
CUCAUCCUAUUUACUGCAGCAAAUCUCUCCUUAGUUGAUGAGACUGUGUUUAUCUCCCUU
UAAAACCCUACCUAUCCUGAAUGGUCUGUCAUUGUCUGCCUUUAAAAUCCUUCCUCUUUC
UUCCUCCUCUAUUCUCUAAAUAAUGAUGGGCUAAGUUAUACCCAAAGCUCACUUUACAA
AAUAUUUCCUCAGUACUUUGCAGAAAACACCAAACAAAAAUGCCAUUUUAAAAAAGGUGU
AUUUUUUCUUUUAGAAUGUAAGCUCCUCAAGAGCAGGGACAAUGUUUUCUGUAUGUUCUA
UUGUGCCUAGUACACUGUAAAUGCUCAAUAAAUAUUGAUGAUGGGAGGCAGUGAGUCUUG
AUGAUAAGGGUGAGAAACUGAAAUCCC
```

The sequence of microRNA-451 (SEQ ID NO:19) is:

```
AAACCGUUACCAUUACUGAGUU
```

The following complex may be formed between microRNA-451 and the relevant region of the YWHAZ mRNA:

```
position 563
                                          (SEQ ID NO: 10)
target   5'  U    U GAUAAG  CAGA        C 3'
             ACUC G      GG     AACGGUU
             UGAG C      CC     UUGCCAA
miRNA    3'  U    U AUUA  A           A 5'
```

Specific embodiments of Blockmirs directed to the microRNA-451 binding site are described in the detailed description with relation to SEQ NO:4.

Example 3

Oligonucleotides for Increasing Insulin Sensitivity

It has been demonstrated that MicroRNA-103/107 inhibition in mice using antimir technology leads to increased insulin sensitivity and signalling (Trajkovski M, 2011). However, microRNA-103/107 inhibition in caveolin-1-deficient mice has no effect on insulin sensitivity and signalling. This is in accordance with earlier reports showing that caveolin-1-deficient mice show insulin resistance and indicate that micro103/107 may affect insulin sensitivity by targeting caveolin-1.

The sequence (SEQ ID NO:11) of the 3'UTR of caveolin is:

```
AUGACAUUUCAAGGAUAGAAGUAUACCUGAUUUUUUUUCCUUUUAAUUUUCCUGGUGCCA
AUUUCAAGUUCCAAGUUGCUAAUACAGCAACAAUUUAUGAAUUGAAUUAUCUUGGUUGAA
AAUAAAAAGAUCACUUUCUCAGUUUUCAUAAGUAUUAUGUCUCUUCUGAGCUAUUUCAUC
UAUUUUUGGCAGUCUGAAUUUUUAAAACCCAUUUAAAUUUUUUUCCUUACCUUUUUAUUU
GCAUGUGGAUCAACCAUCGCUUUAUUGGCUGAGAUAUGAACAUAUUGUUGAAAGGUAAUU
UGAGAGAAAUAUGAAGAACUGAGGAGGAAAAAAAAAAAAAGAAAAGAACCAACAACCUC
AACUGCCUACUCCAAAAUGUUGGUCAUUUUAUGUUAAGGGAAGAAUUCCAGGGUAUGGCC
AUGGAGUGUACAAGUAUGUGGGCAGAUUUUCAGCAAACUCUUUUCCCACUGUUUAAGGAG
UUAGUGGAUUACUGCCAUUCACUUCAUAAUCCAGUAGGAUCCAGUGAUCCUUACAAGUUA
GAAAACAUAAUCUUCUGCCUUCUCAUGAUCCAACUAAUGCCUUACUCUUCUUGAAAUUUU
AACCUAUGAUAUUUUCUGUGCCUGAAUAUUUGUUAUGUAGAUAACAAGACCUCAGUGCCU
UCCUGUUUUUCACAUUUUCCUUUUCAAAUAGGGUCUAACUCAGCAACUCGCUUUAGGUCA
GCAGCCUCCCUGAAGACCAAAAUUAGAAUAUCCAUGACCUAGUUUUCCAUGCGUGUUUCU
GACUCUGAGCUACAGAGUCUGGUGAAGCUCACUUCUGGGCUUCAUCUGGCAACAUCUUUA
UCCGUAGUGGGUAUGGUUGACACUAGCCCAAUGAAAUGAAUUAAAGUGGACCAAUAGGGC
UGAGCUCUCUGUGGGCUGGCAGUCCUGGAAGCCAGCUUUCCCUGCCUCUCAUCAACUGAA
UGAGGUCAGCAUGUCUAUUCAGCUUCGUUUAUUUUCAAGAAUAAUCACGCUUUCCUGAAU
CCAAACUAAUCCAUCACCGGGGUGGUUUAGUGGCUCAACAUUGUGUUCCCAUUUCAGCUG
AUCAGUGGGCCUCCAAGGAGGGGCUGUAAAAUGGAGGCCAUUGUGUGAGCCUAUCAGAGU
UGCUGCAAACCUGACCCCUGCUCAGUAAAGCACUUGCAACCGUCUGUUAUGCUGUGACAC
AUGGCCCCUCCCCCUGCCAGGAGCUUUGGACCUAAUCCAAGCAUCCCUUUGCCCAGAAAG
AAGAUGGGGAGGAGGCAGUAAUAAAAAGAUUGAAGUAUUUUGCUGGAAUAAGUUCAAAU
UCUUCUGAACUCAAACUGAGGAAUUUCACCUGUAAACCUGAGUCGUACAGAAAGCUGCCU
GGUAUAUCCAAAAGCUUUUUAUUCCUCCUGCUCAUAUUGUGAUUCUGCCUUUGGGGACUU
UUCUUAAACCUUCAGUUAUGAUUUUUUUUUCAUACACUUAUUGGAACUCUGCUUGAUUUU
UGCCUCUUCCAGUCUUCCUGACACUUUAAUUACCAACCGUUUACCUACUUUGACUUUUUG
CAUUUAAAACAGACACUGGCAUGGAUAUAGUUUUACUUUUAAACUGUGUACAUAACUGAA
AAUGUGCUAUACUGCAUACUUUUUAAAUGUAAAGAUAUUUUUAUCUUUAUAUGAAGAAAA
UCACUUAGGAAAUGGCUUUGUGAUUCAAUCUGUAAACUGUGUAUUCCAAGACAUGUCUGU
UCUACAUAGAUGCUUAGUCCCUCAUGCAAAUCAAUUACUGGUCCAAAAGAUUGCUGAAAU
```

-continued

UUUAUAUGCUUACUGAUAUAUUUUACAAUUUUUUAUCAUGCAUGUCCUGUAAAGGUUACA

AGCCUGCACAAUAAAAAUGUUUAACGGUU

Targetscan predict the following microRNA-103/107 target in the 3'UTR of cav1:

Position 1141-1147 of CAV1 3' UTR:

```
hsa-miR-107
5'...UGAGCCUAUCAGAGUUGCUGCAA...    (SEQ ID NO: 12)
              |||   ||||||
3' ACUAUCGGGACAUGUU-ACGACGA         (SEQ ID NO: 20)
```

Position 1141-1147 of CAV1 3' UTR:

```
hsa-miR-103
5'...UGAGCCUAUCAGAGUUGCUGCAA...
              |||   |||||
3' AGUAUCGGACAUGUU-ACGACGA          (SEQ ID NO: 21)
```

Other complexes that may be formed between microRNA-103/7 3'UTR of cav1 are listed here:

```
mfe: -24.3 kcal/mol
p-value: undefined
position 1691
target 5'   A           AUU         A 3'        (SEQ ID NO: 13)
              AUGGCUUUGUG   CAAU CUGU
              UAUCGGGACAU   GUUA GACG
miRNA  3' AG                 C    A 5' mfe: -23.9 kcal/mol
p-value: undefined
position 1127
target 5'    G    AU     AGU       A 3'         (SEQ ID NO: 14)
              AGCCU  CAG    UGCUGC
              UCGGG  GUU    ACGACG
miRNA  3' AGUA    ACAU          A 5' mfe: -22.8 kcal/mol
p-value: undefined position 1081
target 5' A   GUG     CCA G  GGG     A 3'       (SEQ ID NO: 15)
           UCA   GGCCU   A GA   GCUGU
           AGU   UCGGG   U UU   CGACG
miRNA  3'  A          ACA G  A      A 5' mfe: -22.0 kcal/mol
p-value: undefined
position 1161
target 5' C  GUAA    ACUUGCAACCG     U       G 3'  (SEQ ID NO: 16)
           UCA   AGC            UCUGU  AUGCUGU
           AGU   UCG            GGACA  UACGACG
miRNA  3'    A                       UGU      A 5' mfe: -21.8 kcal/mol
p-value: undefined
position 1360
target 5'    G           AAA       C 3'         (SEQ ID NO: 17)
              AGUC  GUACAG   GCUGC
              UCGG  CAUGUU   CGACG
miRNA  3' AGUA    GA      A       A 5'
```

Each of these complexes may be blocked using Blockmirs.

Specific embodiments of Blockmirs directed to the microRNA-103/7 binding sites are described in the detailed description in particular with relation to SEQ NO:5 and 6.

REFERENCES

David M. Patrick, C. C.-S. (1. August 2010). Defective erythroid differentiation in miR-451 mutant mice mediated by 14-3ζ. Genes Dev., s. 24: 1614-1619.

Duonan Yu, C. O. (1. August 2010). miR-451 protects against erythroid oxidant stress by repressing 14-3ζ. Genes Dev., s. 24: 1620-1633.

Najafi-Shoushtari SH, K. F. (Science. 2010 May 13. [Epub ahead of print]). MicroRNA-33 and the SREBP Host Genes Cooperate to Control Cholesterol Homeostasis. Science.

Rayner K J, S. Y.-H. (Science. 2010 May 13. [Epub ahead of print]). miR-33 Contributes to the Regulation of Cholesterol Homeostasis.

Trajkovski M, H. J. (June 8; 474(7353): 2011). MicroRNAs 103 and 107 regulate insulin sensitivity. Nature., s. 649-53.

The invention claimed is:

1. A steric block oligonucleotide incapable of recruiting RNase H and RNAi machinery, wherein the oligonucleotide comprises units selected from the group consisting of 2'-O-fluoro units, 2'-O-methoxyethyl, LNA (locked nucleic acid) units, PNA (peptide nucleic acid) units, phosphoramidate units, INA (intercalating nucleic acid), morpholino units, 2'-deoxy-2'-fluoro-arabinonucleic acid (FANA) units, and arabinonucleic acid (ANA) units, and wherein the oligonucleotide comprises a contiguous sequence complementary to at least 12 contiguous bases of SEQ ID NO: 1.

2. The oligonucleotide of claim 1, wherein base pairing includes positions 22-27 of SEQ ID NO: 1.

3. The oligonucleotide of claim 1, wherein the length of the oligonucleotide is between 12 and 22 units and wherein the oligonucleotide is complementary to SEQ ID NO: 1 over its entire length.

4. The oligonucleotide of claim 1, wherein the oligonucleotide does not comprise any RNA units.

5. The oligonucleotide of claim 1, wherein the oligonucleotide does not comprise any DNA units.

6. The oligonucleotide of claim 1, wherein the oligonucleotide comprises LNA units.

\* \* \* \* \*

```
SEQUENCE LISTING

<160> NUMBER OF SEQ ID NOS: 21

<210> SEQ ID NO 1
<211> LENGTH: 40
<212> TYPE: RNA
<213> ORGANISM: Homo sapiens

<400> SEQUENCE: 1
cuauucaaug caaugcaauu caaugcaaug aaaacaaaau                    40

<210> SEQ ID NO 2
<211> LENGTH: 40
<212> TYPE: RNA
<213> ORGANISM: Homo sapiens

<400> SEQUENCE: 2
uguacugaua cuauucaaug caaugcaauu caaugcaaug                    40

<210> SEQ ID NO 3
<211> LENGTH: 40
<212> TYPE: RNA
<213> ORGANISM: Homo sapiens

<400> SEQUENCE: 3
gauacuguac ugauacuauu caaugcaaug caauucaaug                    40

<210> SEQ ID NO 4
<211> LENGTH: 40
<212> TYPE: RNA
<213> ORGANISM: Homo sapiens

<400> SEQUENCE: 4
uuacucugga uaagggcaga aacgguucac auuccauuau                    40

<210> SEQ ID NO 5
<211> LENGTH: 40
<212> TYPE: RNA
<213> ORGANISM: Homo sapiens

<400> SEQUENCE: 5
agcacuugca accgucuguu augcugugac acauggcccc                    40

<210> SEQ ID NO 6
<211> LENGTH: 40
<212> TYPE: RNA
<213> ORGANISM: Homo sapiens

<400> SEQUENCE: 6
auugugugag ccaucagag uugcugcaaa ccugaccccu                     40

<210> SEQ ID NO 7
```

```
<211> LENGTH: 3312
<212> TYPE: RNA
<213> ORGANISM: Homo sapiens

<400> SEQUENCE: 7
agaauccugu cauacgggg uggcugaaag uaaagaggaa cuagacuuuc cuuugcacca      60
ugugaagugu uguggagaaa agagccagaa guugaugugg gaagaaguaa acuggauacu    120
guacugauac uauucaaugc aaugcaauuc aaugcaauga aaacaaaaau ccauuacagg    180
ggcagugccu uuguagccua ugucuuguau ggcucucaag ugaaagacuu gaauuuaguu    240
uuuuaccuau accaugugua aacucuauua uggaacccaa uggacauaug gguuugaacu    300
cacacuuuuu uuuuuuuuuu uguuccugug uauucucauu gggguugcaa caauaauuca    360
ucaaguaauc auggccagcg auuauugauc aaaaucaaaa gguaaugcac auccucauuc    420
acuaagccau gccaugccca ggagacuggu ucccgguga cacauccauu gcuggcaaug     480
agugugccag aguuauuagu gccaaguuuu ucagaaaguu ugaagcacca uggugugaca    540
ugcucacuuu ugugaaagcu gcucugcuca gagucuauca acauugaaua ucaguugaca    600
gaauggugcc augcguggcu aacauccugc uuugauuccc ucugauaagc uguucuggug    660
gcaguaacau gcaacaaaaa uguggggguc uccaggcacg ggaaacuugg uuccauuguu    720
auauugcccu augcuucgag ccaugggucu acagggucau ccuuaugaga cucuaaaaua    780
uacuuagauc cugguaagag gcaaagaauc aacagccaaa cugcuggggc ugcaagcugc    840
ugaagccagg gcaugggauu aaagagauug ugcguucaaa ccuagggaag ccugugccca    900
uuugccuga cugucugcua acauggauca cugcaucuca agauguuuau cugacacaag     960
uguauuauuu cuggcuuuuu gaauuaaucu agaaaaugaa aagauggagu uguauuuuga   1020
caaaaauguu uguacuuuuu aauguuauuu ggaauuuuaa guucuaucag ugacuucuga   1080
auccuuagaa uggccucuuu guagaacccu gugguauaga ggaguauggc cacugcccca   1140
cuauuuuuau uuucuuaugu aaguuugcau aucagucaug acuagugccu agaaagcaau   1200
gugaugguca ggaucucaug acauuauauu ugaguuucuu ucagaucauu uaggauacuc   1260
uuaaucucac uucaucaauc aaauauuuuu ugaguguauc uguagcuga aagaguaugu    1320
acguacguau aagacuagag agauauuaag ucucaguaca cuuccugugc cauguuauuc   1380
agcucacugg uuuacaaaua uagguugucu uguggugua ggagcccacu guaacaauac    1440
ugggcagccu uuuuuuuuu uuuuuuaauu gcaacaaugc aaaagccaag aaaguauaag    1500
ggucacaagu cuaaacaaug aauucuucaa cagggaaaac agcuagcuug aaaacuugcu   1560
gaaaacaca acuuguguuu auggcauuua guaccuucaa auaauggcu ugcagauau      1620
uggauaccc auuaaaucug acagucaa auuuucauc ucuucaauca cuagucaaga       1680
aaaauauaaa aacaacaaau acuuccauau ggagcauuuu ucagaguuuu cuaacccagu   1740
cuuauuuuuc uagucaguaa acauuuguaa aaauacuguu ucacuaauac uuacuguuaa   1800
cugucuugag agaaaagaaa aauaugagag aacuauguu uggggaaguu caagugaucu    1860
uucaauauca uuacuaacuu cuuccacuuu uuccagaauu ugaauauuaa cgcuaaaggu   1920
guaagacuuc agauuucaaa uuaaucuuuc uauauuuuuu aaauuuacag auauuauau    1980
aacccacugc ugaaaagaa aaaaugauu guuuagaag uuaaagucaa uauugauuuu      2040
aaauauaagu aaugaaggca uauuccaau aacuagugau auggcaucgu ugcauuuuac    2100
aguaucuuca aaaauacaga auuuauagaa uaauucuccc ucauuaauaa uuuuucaaaa   2160
ucaaaguuau gguuuccuca uuuuacuaaa aucguauucu aauucuucau uauaguaaau   2220
```

| | |
|---|---|
| cuaugagcaa cuccuuacuu cgguuccucu gauuucaagg ccauauuuua aaaaaucaaa | 2280 |
| aggcacugug aacuauuuug aagaaaacac aacauuuuaa uacagauuga aaggaccucu | 2340 |
| ucugaagcua gaaacaaucu auaguauac aucuucauua auacugguu accuuuaaa | 2400 |
| auaguaauuu uuuacauuuu ccuguguaaa ccuaauugug guagaaauuu uuaccaacuc | 2460 |
| uauacucaau caagcaaaau uucuguauau ucccgugga auguaccuau gugaguuuca | 2520 |
| gaaauucuca aaauacgugu ucaaaaauuu cugcuuuugc aucuuuggga caccucagaa | 2580 |
| aacuuauuaa caacgugaa uaugagaaau acagaagaaa auaauaagcc cucuauacau | 2640 |
| aaaugcccag cacaauucau uguuaaaaaa caaccaaacc ucacacuacu guauuucauu | 2700 |
| aucuguacug aaagcaaaug cuuugugacu auuaaauguu gcacaucauu cauucacugu | 2760 |
| auaguaauca uugacuaaag ccauuugucu uguuuucuu cuugugguug uauauaucag | 2820 |
| guaaaauauu uuccaaagag ccauguguca uguaauacug aaccacuuug auauugagac | 2880 |
| auuaauuugu acccuuguua uuacuacua guauaaugu aauacuguag aaauauugcu | 2940 |
| cuaauucuuu ucaaaauugu ugcauccccc uuagaauguu ucuauuucca uaaggauuua | 3000 |
| gguaugcuau uaucccuucu uauacccuaa gaugaagcug uuuuugugcu cuuuguucau | 3060 |
| cauuggcccu cauuccaagc acuuuacgcu gucuguaaug ggaucuauuu uugcacugga | 3120 |
| auaucugaga auugcaaaac uagacaaaag uuucacaaca gauuucuaag uuaaaucauu | 3180 |
| uucauuaaaa ggaaaaaaga aaaaaaauuu uguaugcaa uaacuuuaua ugaaguauua | 3240 |
| aaaugcauau uucuauguug uaauauaaug agucacaaaa uaaagcugug acaguucugu | 3300 |
| uggucuacag aa | 3312 |

<210> SEQ ID NO 8
<211> LENGTH: 59
<212> TYPE: RNA
<213> ORGANISM: Homo sapiens

<400> SEQUENCE: 8

| | |
|---|---|
| uacugauacu auucaaugca augcauuca augcaaugaa aacaaaauuc cauuacagg | 59 |

<210> SEQ ID NO 9
<211> LENGTH: 2007
<212> TYPE: RNA
<213> ORGANISM: Homo sapiens

<400> SEQUENCE: 9

| | |
|---|---|
| ccggccuucc aacuuuuguc ugccucauuc uaaaauuuac acaguagacc auuugucauc | 60 |
| caugcugucc cacaaauagu uuuuuguuua cgauuuauga cagguuuaug uuacuucuau | 120 |
| uugaauuucu auauuuccca ugugguuuu auguuuaaua uuaggggagu agagccaguu | 180 |
| aacauuuagg gaguuaucug uuucaucuu gagguggcca auauggggau guggaauuuu | 240 |
| uauacaaguu auaaguguuu ggcauaguac uuuugguaca uguggcuuc aaaagggcca | 300 |
| guguaaaacu gcuuccaugu cuaagcaaag aaaacugccu acauacuggu uuguccuggc | 360 |
| ggggaauaaa agggaucauu gguuccaguc acagguguag uaauugugg uacuuuaagg | 420 |
| uuuggagcac uuacaaggcu guguagaau cauaccccau ggauaccaca uauuaaacca | 480 |
| uguauaucug uggaauacuc aauguguaca ccuuugacua cagcugcaga aguguuccuu | 540 |
| uagacaaagu ugugacccau uuacucugg auaagggcag aaacgguuca cauuccauua | 600 |
| uuuguaaagu uaccugcugu uagcuuucau uauuuuugcu acacucauuu uauuuguauu | 660 |

| | |
|---|---|
| uaaauguuuu aggcaaccua agaacaaaug uaaaaguaaa gaugcaggaa aaaugaauug | 720 |
| cuugguauuc auuacuucau guauaucaag cacagcagua aaacaaaaac ccauguauuu | 780 |
| aacuuuuuuu uaggauuuuu gcuuuguga uuuuuuuuu uuugauacuu gccuaacaug | 840 |
| caugugcugu aaaauaaguu aacagggaaa uaacuugaga ugauggcuag cuuuguuuaa | 900 |
| ugucuuauga auuuucaug aacaauccaa gcauaauugu uaagaacacg uguauuaaau | 960 |
| ucauguaagu ggaauaaaag uuuuaugaau ggacuuuuca acuacuuucu cuacagcuuu | 1020 |
| ucauguaaau uagucuuggu ucugaaacuu cucuaaagga aauugacau uuuugaaau | 1080 |
| uuauuccuua uucccucuug gcagcuaaug ggcucuacc aaguuuaaac acaaaauuua | 1140 |
| ucauaacaaa aauacuacua auauaacuac uguuuccaug ucccaugauc cccucucuuc | 1200 |
| cuccccaccc ugaaaaaau gaguuccuau uuuucuggg agagggggg auugauuaga | 1260 |
| aaaaaugua gugguucca uuuaaaauuu uggcauaugg cauuucuaa cuuaggaagc | 1320 |
| cacaauguuc uuggcccauc augacauugg guagcauuaa cuguaaguuu gugcuucca | 1380 |
| aaucacuuuu ugguuuuuaa gaauuucuug uacucuuau agccugccuu caauuuugau | 1440 |
| ccuuuauucu uucuauuugu caggugcaca agauuaccuu ccuguuuuag ccuucugucu | 1500 |
| ugucaccaac cauucuuacu ugguggcau guacuuggaa aaaggccgca ugaucuuucu | 1560 |
| ggcuccacuc agugucuaag gcacccugcu uccuuugcuu gcaucccaca gacuauuucc | 1620 |
| cucauccuau uuacgcagc aaaucucucc uuaguugaug agacugugu uaucccccuu | 1680 |
| uaaaacccua ccuauccuga auggucuguc auugucugcc uuuaaaaucc uuccucuuuc | 1740 |
| uuccuccucu auucucuaaa uaaugauggg gcuaaguuau acccaaagcu cacuuuacaa | 1800 |
| aauauuuccu caguacuuug cagaaaacac caaacaaaaa ugccauuuua aaaaggugu | 1860 |
| auuuuuucu uuagaaugua agccccucaa gagcagggac aauguuuucu guauguucua | 1920 |
| uugugccuag uacacuguaa augcucaaua aauauugaug augggaggca gugagucuug | 1980 |
| augauaaggg ugagaaacug aaauccc | 2007 |

<210> SEQ ID NO 10
<211> LENGTH: 27
<212> TYPE: RNA
<213> ORGANISM: Homo sapiens

<400> SEQUENCE: 10

| | |
|---|---|
| uacucuggau aagggcagaa acgguuc | 27 |

<210> SEQ ID NO 11
<211> LENGTH: 1889
<212> TYPE: RNA
<213> ORGANISM: Homo sapiens

<400> SEQUENCE: 11

| | |
|---|---|
| augacauuuc aaggauagaa guauaccuga uuuuuuuucc uuuuaauuuu ccuggugcca | 60 |
| auuucaaguu ccaaguugcu aauacagcaa caauuuauga auugaauuau cuggguugaa | 120 |
| aauaaaaaga ucacuuucuc aguuuucaua aguauuaugu cucuucugag cuauuucauc | 180 |
| uauuuuggc agucugaauu uuuaaaaccc auuuaaauuu uuuuccuuac cuuuuuauuu | 240 |
| gcaugugau caaccaucgc uuuauggcu gagauaugaa cauauuguug aaagguaauu | 300 |
| ugagagaaau augaagaacu gaggaggaaa aaaaaaaaaa agaaaagaac caacaaccuc | 360 |
| aacugccuac uccaaaaugu uggucauuuu auguuaaggg aagaauucca ggguauggcc | 420 |
| auggagugua caaguaugug ggcagauuuu cagcaaacuc uuuucccacu guuuaaggag | 480 |

```
uuaguggauu acugccauuc acuucauaau ccaguaggau ccagugaucc uuacaaguua    540
gaaaacauaa ucuucugccu ucucaugauc caacuaaugc cuuacucuuc uugaaauuuu    600
aaccuaugau auuuucugug ccugaauauu uguuauguag auaacaagac cucagugccu    660
uccuguuuuu cacauuuucc uuuucaaaua gggucuaacu cagcaaucug cuuuaggucu    720
gcagccuccc ugaagaccaa aauuagaaua uccaugaccu aguuuccauu gcguguuucu    780
gacucugagc uacagagucu ggugaagcuc acuucugggc uucaucuggc aacaucuuua    840
uccguagugg guaugguuga cacuagccca augaaaugaa uuaagugga ccaauagggc     900 ugagcucucu ugggcuggc aguccuggaa gccagcuuuc ccugccucuc aucaacugaa     960
ugaggucagc augucuauuc agcuucguuu auuuucaaga auaaucacgc uuccugaau    1020 ccaaacuaau ccaucaccgg gguguuuag uggcucaaca uugugucccc auucagcug     1080 aucagugggc cuccaaggag gggcuguaaa auggaggcca uguguggagc cuaucagagu    1140
ugcugcaaac cugacccug ucaguaaag cacuugcaac cgucuguuau gcugugacac     1200
auggccccuc ccccugccag gagcuuugga ccuaauccaa gcaucccuuu gcccagaaag    1260
aagauggggg aggaggcagu aauaaaaaga uugaaguauu uugcuggaau aaguucaaau    1320
ucuucugaac ucaaacugag gaauuucacc uguaaaccug agcguacag aaagcugccu     1380 gguauaucca aaagcuuuuu auccuccug cucauauugu gauucugccu uuggggacuu     1440
uucuuaaacc uucaguuaug auuuuuuuu cauacacuua uuggaacucu gcuugauuuu     1500
ugccucuucc agucuuccug acacuuuaau uaccaaccug uuaccuacuu gacuuuuug    1560 cauuuaaaac agacacuggc auggauauag uuuuacuuuu aaacgugua cauaacugaa    1620 aaugugcuau acugcauacu uuuuaaaugu aaagauauuu uuaucuuuau augaagaaaa    1680
ucacuuagga aauggcuuug ugauucaauc uguaaacugu guauuccaag acaugucugu    1740
ucuacauaga ugcuuagucc ucaugcaaa ucauuacug guccaaaaga uugcugaaau     1800
uuuauaugcu uacugauaua uuuuacaauu uuuuucaug caugccugu aaagguuaca     1860 agccugcaca auaaaaaugu uuaacgguu                                     1889
```

<210> SEQ ID NO 12
<211> LENGTH: 23
<212> TYPE: RNA
<213> ORGANISM: Homo sapiens

<400> SEQUENCE: 12
ugagccuauc agaguugcug caa                                              23

<210> SEQ ID NO 13
<211> LENGTH: 24
<212> TYPE: RNA
<213> ORGANISM: Homo sapiens

<400> SEQUENCE: 13
aauggcuuug ugauucaauc ugua                                             24

<210> SEQ ID NO 14
<211> LENGTH: 21
<212> TYPE: RNA
<213> ORGANISM: Homo sapiens

<400> SEQUENCE: 14
gagccuauca gaguugcugc a                                                21

```
<210> SEQ ID NO 15
<211> LENGTH: 28
<212> TYPE: RNA
<213> ORGANISM: Homo sapiens

<400> SEQUENCE: 15
aucagugggc cuccaaggag gggcugua                                          28

<210> SEQ ID NO 16
<211> LENGTH: 36
<212> TYPE: RNA
<213> ORGANISM: Homo sapiens

<400> SEQUENCE: 16
cucaguaaag cacuugcaac cgucuguuau gcugug                                 36

<210> SEQ ID NO 17
<211> LENGTH: 20
<212> TYPE: RNA
<213> ORGANISM: Homo sapiens

<400> SEQUENCE: 17
gagucguaca gaaagcugcc                                                   20

<210> SEQ ID NO 18
<211> LENGTH: 21
<212> TYPE: RNA
<213> ORGANISM: Homo sapiens

<400> SEQUENCE: 18
gugcauugua guugcauugc a                                                 21

<210> SEQ ID NO 19
<211> LENGTH: 22
<212> TYPE: RNA
<213> ORGANISM: Homo sapiens

<400> SEQUENCE: 19
aaaccguuac cauuacugag uu                                                22

<210> SEQ ID NO 20
<211> LENGTH: 23
<212> TYPE: RNA
<213> ORGANISM: Homo sapiens

<400> SEQUENCE: 20
agcagcauug uacagggcua uca                                               23

<210> SEQ ID NO 21
<211> LENGTH: 23
<212> TYPE: RNA
<213> ORGANISM: Homo sapiens

<400> SEQUENCE: 21
agcagcauug uacagggcua uga                                               23
```